United States Patent [19]

Gozzo et al.

[11] 4,442,301

[45] Apr. 10, 1984

[54] PROCESS FOR STEREOSELECTIVELY SYNTHESIZING CYCLOPROPANE CARBOXYLATES

[75] Inventors: Franco Gozzo; Giuseppe Caprara; Lamberto Roberti; Giuseppe Paparatto; Ettore Santoro, all of Milan, Italy

[73] Assignee: Montedison S.p.A., Milan, Italy

[21] Appl. No.: 278,676

[22] Filed: Jun. 29, 1981

[30] Foreign Application Priority Data

Jul. 2, 1980 [IT] Italy .............................. 23180 A/80

[51] Int. Cl.³ .......................................... C07C 69/743
[52] U.S. Cl. ..................................... 560/124; 560/213
[58] Field of Search ........................................ 560/124

[56] References Cited

U.S. PATENT DOCUMENTS

| 4,243,677 | 1/1981 | Engel | 560/124 |
| 4,252,820 | 2/1981 | Lantzsch | 560/124 |
| 4,258,202 | 3/1981 | Piccardi | 560/124 |
| 4,330,675 | 5/1982 | Huff | 560/124 |

FOREIGN PATENT DOCUMENTS

53-40741  4/1978  Japan .................................. 560/124

Primary Examiner—Michael L. Shippen
Attorney, Agent, or Firm—Morgan, Finnegan, Pine, Foley & Lee

[57] ABSTRACT

A process for stereospecifically synthesizing lower alkyl esters of the cis-2,2-dimethyl-3-($\beta$-fluoro-$\beta$-trifluoromethyl-vinyl)-cyclopropanecarboxylic acid.

15 Claims, No Drawings

PROCESS FOR STEREOSELECTIVELY SYNTHESIZING CYCLOPROPANE CARBOXYLATES

This invention relates to a process for stereoselectively synthesizing intermediates for pyrethroids and, more particularly, to a two-step process forstereoselectively synthesizing lower alkyl esters of the cis2,2-dimethyl-3-($\beta$-fluoro-$\beta$-trifluoromethyl-vinyl)-cyclo-propropanecarboxylic acid.

The cis isomerism in the cyclopropane ring is the one which generally imparts the highest insecticide activity to synthetic pyrethroids, wherefore considerable efforts have been made in the research field with a view to isolating cis isomers or at least to obtaining mixtures enriched in the cis isomer.

The known stereoselective syntheses of pyrethroids or intermediate thereof, however, are limited and exclusively concern the synthesis of 2,2-dimethyl-cyclopropane carboxylates having a $\beta,\beta$-dihalovinyl group in position 3.

Out of these syntheses we may cite the synthesis described in French Pat. No. 1,580,474 (Roussel Uclaf), which provides a lactone of formula:

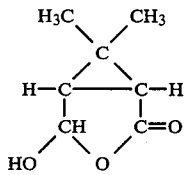

which is then reacted with a phosphorous ylide according to the Wittig reaction.

The abovesaid lactone is prepared in a somewhat complicated and expensive manner starting from lower alkyl esters of caronaldehyde (2,2-dimethyl-3-formyl-cyclopropane carboxylic acid).

Other examples of stereoselective syntheses, limited as well to the preparation of 2,2-dimethyl-3-($\beta,\beta$-dihalo-vinyl)-cyclopropane carboxylates, are described in "Synthetic Pyrethroids", ACS Symposium Series No. 42—M. Elliott Editor—Washington 1977.

Published British patent applications No. 2,000,764 (Imperial Chemical Industries) and No. 2,015,519 (in the name of the same Applicant) relate to pyrethroids which, among others, are comprised in the following general formula:

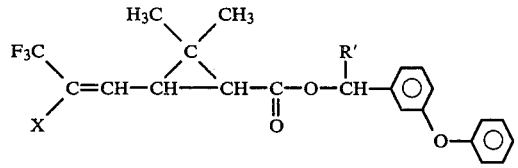

wherein X is halogen and R'=H, CN, —C≡CH.

In the first British patent application, compounds of formula I, in which X is Cl or Br, have been exemplified; in the latter, compounds of formula I, in which X is F, Cl or Br.

Intermediates for preparing pyrethroids of general formula I are the lower alkyl esters of formula:

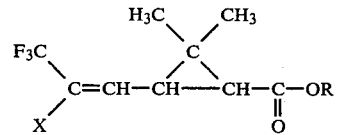

where X is halogen, and R is a lower alkyl.

One of the processes for synthesizing the intermediates of formula II which is described in the abovesaid patent applications consists in dehydrohalogenating, in the presence of a base, compounds of formula:

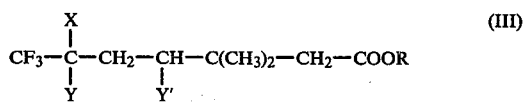

(wherein Y and Y'=Cl or Br according to British patent application No. 2,015,519; Y and Y'=F, Cl or Br according to British patent application No. 2,000,764).

Dehydrohalogenation is substantially conducted by treating the compounds of formula III with two equivalents of a base in a suitable solvent.

In British patent application No. 2,000,764, there is generally specified that suitable bases are tertiary amines or alkali alkoxides, particularly suited being the system consisting of an alkali alkoxide and of the corresponding alcohol as solvent. In the only example described in detail in said patent application, sodium-tert-butoxide in tetrahydrofuran is employed as a base.

In British patent application No. 2,015,519, alkaline hydrides or alkoxides or acid-accepting amines in polar solvents are mentioned as bases.

There are exemplified dehydrohalogenation reactions conducted by employing NaOC$_2$H$_5$ in ethanol or in N,N-dimethyl-formamide.

As probable intermediates which form during the dehydrohalogenation reaction of the compounds of formula III there are indicated, in both the abovesaid patent application, the compounds of formulas:

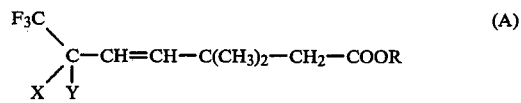

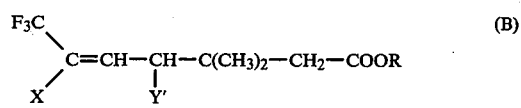

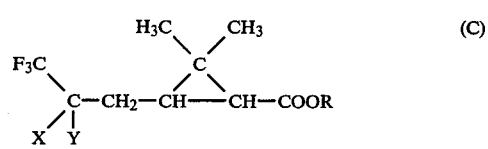

British patent application No. 2,015,519 describes how to prepare compounds of formula C (X=Y=Br) by dehydrohalogenation of the corresponding compound of formula III under controlled conditions (low conversion, absence of a base, NaOC$_2$H$_5$ in ethanol, temperatures ranging from 19° to 23° C.).

Besides the abovesaid product also products of further dehydrohalogenation are obtained.

British patent application No. 2,000,764 describes, but does not exemplify, the possibility of obtaining compounds of formula II by dehydrohalogenation with a base of compounds of formula A, B or C, but nothing is specified about the forming of single isomers.

It is important to point out that in both abovesaid British applications there is indicated that the process therein described permits to obtain the compounds of formula II as mixtures of cis and trans isomers.

From the examples contained in said patent applications one can notice that the ratio between cis isomers and trans isomers is close to unity.

According to what is described in the aforesaid British patent applications, the only known method of obtaining an individual isomer of the compounds of formula II consists in separating it from the isomeric mixture by means of column chromatography or fractional crystallization of the carboxylic acids derived from the esters of formula II.

Such techniques are expensive due to the time required, the materials utilized (particular solvents, chromatographic substrata, etc.) and chiefly due to the undesired isomers which must be removed and to the lower yield of the isomer to be obtained.

Stereoselective processes for synthesizing the compounds of formula II are neither mentioned in the aforesaid British patent applications, nor, to applicants' knowledge, have been described elsewhere.

The term "stereoselective", whenever used herein, designates a reaction leading to the predominant formation of one out of the two possible steric isomers, in particular the cis isomer on the cyclopropane ring of the lower alkyl esters of the 2,2-dimethyl-3-($\beta$-fluoro-$\beta$-trifluoromethyl-vinyl)-cyclopropane carboxylic acid (compounds of formula II, wherein X is F). "Predominant formation" of the cis isomer means that, in the mixture of the two cis and trans isomers, the cis isomer constitutes at least 70% of said mixture.

We have surprisingly found that by effecting the dehydrohalogenation of compounds of formula III in which X is F and Y' is Br (hereinafter referred to as III-F) under the conditions specified hereinafter, it is possible to obtain, in a highly selective manner, the corresponding compounds of formula A almost free from compounds of types B and C.

We have still more surprisingly found that the dehydrohalogenation of compounds A, wherein X is F (hereinafter referred to as A'), under the conditions specified hereinbelow, leads to the stereoselective formation of compounds of formula II in which X is F (hereinafter referred to as II-F) in cis form.

Thus it is an object of the present invention to provide a two-step stereoselective process for synthesizing the cis isomers of the compounds of formula II-F consisting in dehydrohalogenating, in the presence of primary or secondary amines and in a non-polar solvent, the compounds of formula III-F, obtaining, with a high selectivity, the compounds of formula A', and further consisting in dehydrohalogenating said compounds of formula A', in the presence of an alkaline base and in a substantially non-polar such as an ether.

The process forming the object of this invention can be schematically represented as in the following scheme 1.

Scheme 1

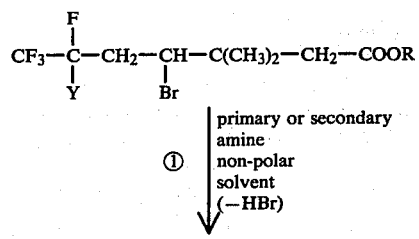

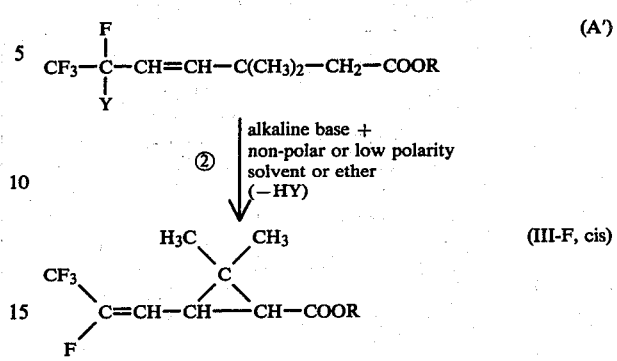

[Y is Cl or Br; R is a lower alkyl]. The first step of the process (reaction 1, scheme 1) is conducted by dehydrohalogenating the compound of formula III-F, in which substituent Y is an atom of chlorine or of bromine (preferably bromine), by means of a primary or secondary amine, preferably a secondary cyclic amine, and in a non-polar or low polarity non-polar solvent. The temperature at which the reaction occurs is not critical. It can range from 0° C. to the boiling temperature of the solvent. For practical purposes it is preferable to operate at the boiling temperature of the solvent in order to cause the reaction to occur more rapidly.

Operating under the above-mentioned experimental conditions, reaction 1 proves to be highly selective in so far as the products of type C are practically absent and, out of the products A' and B' (compound B'=compound B in which X is F), compound A' makes up at least 80% of the mixture (ratio A':B>4.9).

When it is operated out of the abovesaid conditions, the dehydrohalogenation of adduct III-F does not lead to a satisfactory A':B' ratio (see example 3).

If, for example, instead of a primary or secondary amine, a tertiary amine, such as pyridine or triethylamine, in a substantially non-polar solvent is employed as a base, the reaction does not occur at appreciable rates and no formation of any product is observed.

In a polar solvent, the action of a tertiary amine leads to the predominant formation of compound B'.

If it is operated in an excess of pyridine, which so acts as a base and as a polar solvent, an A':B' ratio lower than 1 is obtained.

When the dehydrohalogenation of adduct III-F is effected by exclusively employing a very strong base (alkaline hydroxides, acetates or alcoholates), besides products of type C, also products A' and B' in comparable amounts are obtained (A':B' ratio about equal to 1).

As secondary amines suitable for being employed in reaction 1 we may cite: piperidine, pyrrolidine, morpholine, piperazine, tetramethylguanidine, etc., or also mixtures of various secondary amines.

As non-polar solvents we may cite aliphatic hydrocarbons or cycloaliphatic hydrocarbons, aromatic and alkyl aromatic hydrocarbons.

As low-polarity solvents suited to Reaction 1 we may cite ethers, including cyclic ethers, and alcohols.

The importance of the polarity of the solvent in which reaction 1 is caused to take place is evidenced by the results of the tests described in example 3 (Table 1).

In fact, when the same base (piperidine) is used, but if the reaction is carried out in solvents of increasing polarity [n-hexane ($\epsilon_{20.}=1.89$); ethyl alcohol ($\epsilon_{25.}=24.3$)], a decrease in the A':B' ratio from 31 (n-hexane) to 5 (ethyl alcohol) is obtained as a result.

The amount of amine utilized for effecting the selective monodehydrohalogenation of the compounds of formula III-F may be stoichiometric or in excess. Another possibility consists in employing an amine in catalytic amounts, namely in an amount considerably less with respect of the amount of halogenhydric acid (H Y) to be neutralized.

In such case it is sufficient to effect the dehydrohalogenation in the presence of an alkaline base in at least a stoichiometric amount with respect of the acid to be neutralized. As a halogenhydric acid-accepting alkaline base it is possible to use a hydroxide, a salt having an alkaline reaction or a hydride.

When the base is an alkaline hydroxide, this may be used in aqueous solution; when the base is an alkaline hydride, such hydride may be used as a suspension in a suitable reaction solvent.

A two-phase system is thus obtained which consists of an organic phase (non-polar solvent, compound of formula III-F, and secondary amine) and of an aqueous phase (water and alkaline base), or of a solid phase (alkaline hydride). As the reaction proceeds, the amine is restored from the salt that has formed, by the alkaline base, wherefore it exerts a catalytic activity.

According to a practical embodiment, reaction 1 is conducted by simply mixing the organic solvent with the base and with the compound of formula III-F and by heating, under stirring, the reaction mixture at the reflux temperature of the solvent. After a few hours, a high conversion of the compound of formula III-F is obtained.

From the resulting mixture (in which compound A' constitutes the predominant part) it is possible to obtain, after washing with alkaline and acid water followed by separation of the organic phase, anhydrification and distillation, the compound of type A' with high yields and a high degree of purity.

If it is operated in the presence of a two-phase system, the reaction conditions are analogous.

The second step of the process (Reaction 2) consists in the dehydrohalogenation of compound A' obtained from step 1.

In order to obtain compounds of formula II-F with a high stereoselectivity with respect to the cis isomers, it is important to employ low polarity solvents such as ethers, or preferably, non-polar solvents.

The dehydrohalogenation of compound A' conducted in the presence of at least stoichiometric amounts of alkaline bases and in a non-polar solvent or in ether, leads to the stereoselective formation of the cis isomer of the compounds of formula II-F.

By increasing the polarity of the solvent, the cis-trans ratio decreases.

The reaction temperature is not critical when non-polar solvents are used and, in this case, it is therefore possible to operate at a temperature between 0° C. and the reflux temperature of the solvent, the latter being preferred for practical purposes.

Conversely, when the dehydrohalogenation of compound A' is carried out in ethers, the temperature plays a critical role since, by operating at temperatures higher than 50° C., the cis/trans ratio decreases and, consequently, the stereoselectivity of reaction 2 decreases (see example 6).

Inorganic bases suited for use in reaction 2 are alkaline alcoholates or alkaline hydrides in the presence of alcoholates. Particularly suited is the use, for example, of at least a stoichiometric amounts of an alkaline hydride in the presence of a catalytic amount of an alcoholate prepared "in situ" by addition of a little amount of the corresponding alcohol.

As non-polar solvents suited for use in reaction 2 we may cite aliphatic, cycloaliphatic, aromatic and alkylaromatic hydrocarbons.

Other solvents which may be used are the ethers, both the aliphatic and the alicyclic ones provided, as mentioned hereinbefore, that the reaction temperatures does not exceed 50° C.

The reaction is conducted by mixing the solvent, the alkaline base and the compound of formula A' and by stirring the reaction mixture at the reflux temperature of the solvent, in the case of non-polar solvents, or at a temperature lower than 50° C. if an ether is used as a solvent.

After a few hours a high conversion degree of compound A' is obtained.

From the reaction mixture, after neutralization, the salt which has formed is separated and, by distillation, the cyclization product is also separated.

Thus, the cis isomer of the compounds of formula II-F is stereoselectivity obtained.

Due to the presence of a double bond, the compounds of formula II-F may exist in the form of isomers E and Z (isomerism on the double bond).

By virtue of the high selectivity of reaction 1 also at high conversion percentages, it is possible to carry out the process forming the object of the present invention also according to a variation which proves particularly useful for practical purposes.

Said variation consists in carrying out reactions 1 and 2 without isolating compound A'.

In this case, after having conducted reaction 1 according to the above-mentioned conditions, the resulting reaction mixture is added with the necessary amount of inorganic base, whereupon it is isolated in accordance with what has been described for reaction 2.

Thus, the process object of this invention allows to obtain, in a stereoselective way, the cis isomers of the cyclopropane carboxylic acids of formula II-F.

For the practical purposes to which said compounds are used, i.e. for preparing insecticide pyrethroids, the little amount of trans isomer which may be present does not have particular importance. Therefore the mixture so obtained (of which the cis isomer makes up the by far prevailing portion) can be utilized without any further separations for the successive reactions aiming at preparing pyrethroids.

The following examples are given to better illustrate the present invention.

EXAMPLE 1

Preparation of compound ethyl-3,3-dimethyl-6-bromo-6,7,7,7-tetrafluoro-hept-4-enoate[compound A', Y=Br, R=$C_2H_5$]

Into a flask equipped with a reflux condenser and a stirrer there were introduced:

0.1 moles of ethyl-3,3-dimethyl-4,6-dibromo-6,7,7,7-tetrafluoro-heptanoate $CF_3$—CFBr—$CH_2$—CHBr—C($CH_3$)$_2$—$CH_2$—COO$C_2H_5$ (prepared as described in British patent application No. 2,015,519) [Compound III-F, Y=Br, R=C₂H₅].
0.13 moles of piperidine,
200 ml of toluene.

The reaction mixture was heated under reflux conditions for 2 hours. After cooling, the organic phase was washed with acid water and successively with a NaOH solution at 10%, then with water up to a neutral pH, and dried over anhydrous Na₂SO₄.

The gas chromatographic analysis (GLC) of a sample of the organic solution revealed an almost complete disappearance of the starting product and the presence of a new product at a concentration of about 88% calculated on the basis of the ratio of the areas of the gas chromatographic peaks. The identity of this compound with the product to be obtained was proved after its separation was carried out according to the following modalities.

The organic solution was distilled at reduced pressure, collecting the fraction which distilled between 52.5° and 55° C. at 0.5 mm Hg (25 g).

Said fraction resulted to consist of the desired product having a purity degree higher than 95%, the only impurity present therein being represented by the isomer of type B' (Ratio A':B'>19.

The elemental analysis was consistent with the assigned structure.

IR (infrared spectroscopy): significant bands at 1740 cm⁻¹ ($\nu$C=O) and 1665 cm⁻¹ ($\nu$C=C).

1H NMR (Nuclear magnetic resonance) (CDCl₃, TMS); CF₃—CFBr—CH$_a$=CH$_B$—C (CH₃)₂—CH₂—COOC₂H₅; $\delta H_A$=5.7 ppm; $\delta H_B$=6.3 ppm; $J_{H_A\text{-}H_B}$=14.9 Hz; $J_{H_A\text{-}F}$=17.7 Hz.

EXAMPLE 2

The reaction of example 1 was repeated employing a two-phase system.

Into a flask equipped with a reflux condenser and a stirrer there were introduced.

0.1 moles of ethyl 3,3-dimethyl-4,6-dibromo-6,7,7,7-tetra-fluoro-heptanoate,
2 ml of piperidine,
100 ml of benzene,
0.2 moles of NaOH in 10 ml of water.

The reaction mixture was maintained at reflux for 7 hours. After cooling, a sample of the organic phase, when subjected to gas chromatographic analysis, revealed the complete disappearance of the starting ester and the appearance of only one peak corresponding to the compound ethyl 3,3-dimethyl-6-bromo-6,7,7,7-tetrafluoro-hept-4-enoate.

After separation of the two phases, drying of the organic phase and removal of the solvent by distillation under reduced pressure, 30 g of product having a gas chromatographic titre of about 90% were obtained (yield referred to the impure product=about 80%).

EXAMPLE 3

The test conditions and the results of monodehydrohalogenation tests of the compound ethyl-3,3-dimethyl-4,6-dibromo-6,7,7,7-tetrafluoro-heptanoate, according to the present invention, as well as comparative tests are recorded on the following Table 1.

The operating conditions are analogous to the ones of example 1. The tests from 3.1 to 3.6 evidence the high selectivity of reaction 1 towards compound A', when primary or secondary amines and low polarity solvents are employed.

The products obtained from the reactions 3.1 to 3.6 are free from cyclopropanecarboxylic derivatives and in the mixture of A' and B' compound A' constitutes the highly prevailing percentage, since it ranges from 84% (test 3.3, ratio A'/B'=5) to 97% (test 3.1, ratio A'/B'=31).

Tests 3.7 and 3.8 show how very low conversion rates are attained when tertiary amines in non-polar solvents are used.

If tertiary amines are employed in polar solvents (test 3.9), the conversion rate is high, but the ratio A'/B' is disadvantageous (A'/B'=0.35).

The A'/B' ratio results disadvantageous also when a hydroxide or an alkaline salt in the presence of phase-transfer catalysts are employed as a base (tests 3.10 and 3.11).

Tests 3.12 and 3.13 conducted under conditions analogous to those described in the previously cited British patent applications show how, in this case, the reaction proceeds until there are obtained cyclopropane carboxylates with an isomeric cis-trans ratio unity.

TABLE 1

Dehydrohalogenation of compound CF₃—CFBr—CH₂—CHBr—C(CH₃)₂—CH₂—COOC₂H₅

| Test No. | Base | Base moles/ compound moles | Solvent | Temperat. (°C.) | Time (h) | Conversion (%) | Ratio[1] A/B | Cyclopropane[2] carboxylic derivatives (%) |
|---|---|---|---|---|---|---|---|---|
| 3.1 | piperidine | 1,5 | n-hexane | 70 | 8 | 88 | 31 | — |
| 3.2 | piperidine | 1,5 | THF[3] | 67 | 3 | 83 | 8,6 | — |
| 3.3 | piperidine | 1,5 | ethyl alcohol | 78 | 3 | 88 | 5 | — |
| 3.4 | morpholine | 2 | toluene | 110 | 6 | 84 | 25 | — |
| 3.5 | pyrrolidine | 2 | n-hexane | 70 | 7 | 94 | 17 | — |
| 3.6 | n-butylamine | 2 | toluene | 110 | 9 | 80 | 9 | — |
| 3.7 | tributylamine | 2 | n-hexane | 70 | 6 | 0 | — | — |
| 3.8 | pyridine | 2 | benzene | 81 | 6.5 | 5 | <1 | — |
| 3.9 | pyridine | excess | pyridine | 115 | 2 | 95 | 0.35 | — |
| 3.10 | KBH/TBA[4] | 2 | benzene | 50 | 3 | 76 | 1 | traces |
| 3.11 | KOAc/TBA[4] | 3 | H₂O | boiling | 15 | 85 | 0.7 | traces |
| 3.12 | NaOC₂H₅ | 3 | C₂H₅OH | 0 | 1 | 85 | 2.2 | 54[5] |

TABLE 1-continued

Dehydrohalogenation of compound $CF_3$—$CFBr$—$CH_2$—$CHBr$—$C(CH_3)_2$—$CH_2$—$COOC_2H_5$

| Test No. | Base | Base moles/ compound moles | Solvent | Temperat. (°C.) | Time (h) | Conversion (%) | Ratio[1] A/B | Cyclopropane[2] carboxylic derivatives (%) |
|---|---|---|---|---|---|---|---|---|
| 3.13 | $NaOC_2H_5$ | 3 | THF[3] | 66 | 0.25 | 100 | —[6] | 99[7] |

Notes to Table 1
[1]Compound A' = $CF_3$—$CFBr$—$CH$=$CH$—$C(CH_3)_2$—$CH_2$—$COOC_2H_5$
Compound B' = $CF_3$—$CF$=$CH$—$CHBr$—$C(CH_3)_2$—$CH$—$COOCH_2H_5$
[2]Compounds of type C and of formula II
[3]THF = tetrahydrofuran
[4]TBA = tetrabutylammonium bromide
[5]Cyclopropane carboxylates with prevailingly trans isomerism.
[6]Products A' and B' are present in traces
[7]Ethyl 2,2-dimethyl-3-(β-trifluoromethyl-β-fluoro-vinyl)-cyclopropane carboxylate with a ratio of cis-trans isomers (in the cyclopropane ring) equal to 46:54.

EXAMPLE 4

Stereoselective preparation of the cis isomer (on the cyclopropane ring) of compound ethyl 2,2-dimethyl-3-(β-fluoro-β-trifluoromethyl-vinyl)-cyclopropane carboxylate [II-F, R=$C_2H_5$].

A flask equipped with a reflux condenser and a stirrer was charged with:
0.04 moles of NaH in 30 ml of n.hexane.
After having brought at reflux there were added:
0.02 moles of ethyl 3,3-dimethyl-6-bromo-6,7,7,7-tetrafluoro-hept-4-enoate (prepared as described in example 1) in
20 ml of n-hexane
0.15 ml of ethyl alcohol.

The reaction mixture was kept under stirring at reflux temperature for 5 hours.

After cooling, a sample of the organic phase was subjected to gas chromatographic analysis: it revealed that the starting ester was quantitatively converted, thus providing the desired product with a ratio of cis:trans isomers equal to 82:18 (isomerism on the ring).

After neutralization, the organic phase was distilled at reduced pressure in order to remove the solvent, so obtaining a residue consisting of 4.6 g of the desired product with a purity of 82%, the remaining portion being the trans isomer.

EXAMPLE 5

By operating as described in example 4, but employing, as a base, sodium ethoxide ($NaOC_2H_5$) instead of sodium hydride, it was possible to obtain, after a 2-hour reaction at 45° C., a conversion of the starting product eaual to 93%. After working up the reaction mixture, 4.6 g of a mixture were obtained, the composition of which (determined by GLC) was the following:
- 91% of ethyl 2,2-dimethyl-3-(β-trifluoromethyl-β-fluoro-vinyl)-cyclopropane carboxylate (cis:trans ratio=82.6:17.4),
- 6.9% of unconverted starting product,
- 2.1% of other unidentified products.

EXAMPLE 6

The test conditions and the results of dehydrohalogenation tests of the compound ethyl 3,3-dimethyl-6-bromo-6,7,7,7-tetra-fluoro-hept-4-enoate according to the present invention and of comparative tests are recorded on the following Table 2.

In all the tests recorded on Table 2, sodium ethylate ($NaOC_2H_5$) was employed as a base.

The ratio between cis and trans isomers in the dehydrohalogenation product [ethyl 2,2-dimethyl-3-(β-trifluoromethyl-β-fluoro-vinyl)-cyclopropane] was determined by means of gas chromatographic analysis (GLC). Tests 6.1 to 6.7, according to this invention, evidence the stereoselectivity towards this cis isomer, both in non-polar solvents (6.1–6.4) and in ethers (6.5–6.7) provided that, in the latter case, a temperature of 50° C. (see test 6.8) is not exceeded. Tests 6.9 and 6.10 evidence how the same reaction, if conducted in highly polar solvents, even at low temperature, is not stereoselective.

TABLE 2

Dehydrohalogenation of compound
$CF_3$—$CFBr$—$CH$=$CH$—$C(CH_3)_2$—$CH_2$—$COOC_2H_5$
with $NaOC_2H_5$

| Test No. | Solvent | Temperature (°C.) | Reaction time | Conversion (%) | Ratio cis/trans in the dehydrohalogenation product[1] |
|---|---|---|---|---|---|
| 6.1 | Benzene | 20 | 18 h. | 98 | 5 (83:17) |
| 6.2 | Benzene | 60 | 2 h | 100 | 4,6 (82:18) |
| 6.3 | n-hexane | 35 | 2 h | 80 | 5,8 (85:15) |
| 6.4 | n-hexane | 60 | 2 h | 100 | 3,3 (77:23) |
| 6.5 | Diethylether | 20 | 24 h | 88 | 4,6 (82:18) |
| 6.6 | THF[2] | 0 | 2 h | 100 | 2,5 (71:29) |
| 6.7 | THF | 30 | 10 min. | 97 | 2,6 (72:28) |
| 6.8 | THF | 60 | 10 min. | 100 | 1,8 (65:35) |
| 6.9 | DMF[3] | 0 | 15 min. | 63 | 1,1 (52:48) |
| 6.10 | DMF | 20 | 1,5 h | 92 | 1,18 (54:46) |

Note to Table 2:
[1]Dehydrohalogenation product: ethyl 2,2-dimethyl-3-(β-trifluoromethyl-β-fluoro-vinyl)-cyclopropane carboxylate (cis and trans on the ring)

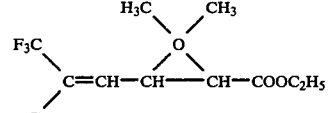

[2]THF = tetrahydrofuran
[3]DMF = dimethylformamide.

EXAMPLE 7

It is the object of this example to describe the stereoselective preparation of the cis isomer of ethyl 2,2-dimethyl-3-(β-trifluoromethyl-β-fluoro-vinyl)-cyclopropane carboxylate starting from ethyl 3,3-dimethyl-4,6-dibromo-6,7,7,7-tetrafluoro-heptanoate (1)
[$CF_3$—$CFBr$—$CH_2$—$CHBr$—$C(CH_3)_2$—$CH_2$—$COOC_2H_5$] without isolating the intermediate ethyl 3,3-dimethyl-6-bromo-6,7,7,7-tetrafluoro-hept-4-enoate (2)
[$CF_3$—$CFBr$—$CH$=$CH$—$C(CH_3)_2$—$COOC_2H_5$].

Into a flask equipped with a stirrer and a reflux condenser were introduced:
0.02 moles of NaH in 20 ml of n.hexane
0.015 moles of piperidine After having heated the mixture at reflux under stirring, 0.01 moles of $CF_3$—$CFBr$—$CH_2$—$CHBr$—$C(CH_3)_2$—$CH_2$—$COOC_2H_5$ (1) in 10 ml of n.hexane were rapidly added.

The reaction mixture was maintained under stirring at reflux temperature for 7 hours.

After cooling, a sample of the organic phase subjected to gas chromatographic analysis revealed the following composition:

10% of unreacted compound (1),
86% of compound (2),
4% of other compounds.

0.02 moles of NaH were then added to the reaction mixture. After having heated the reaction mixture again at reflux, 0.3 ml of ethyl alcohol were added and the mixture was stirred and maintained at reflux for 1 hour. After cooling, a sample of the mixture, analyzed by gas chromatography, revealed to be composed by ehtyl 2,2-dimethyl-3-($\beta$-trifluoromethyl)-$\beta$-fluorovinyl)-cyclopropane carboxylate (cis:trans ratio=81:19). while compound (1) and intermediate (2) were absent. The reaction mixture was then repeatedly washed with water and dried. The solvent was removed by evaporation at reduced pressure, thus so obtaining 2 g of a residue consisting of the abovesaid cyclopropane carboxylic ester (cis:trans on the ring=81:19) and having a titre higher than 95% (GLC).

EXAMPLE 8

Object of this example is to describe the preparation of the analytically pure cis isomer of the compound ethyl 2,2-dimethyl-3-($\beta$-trifluoromethyl-$\beta$-fluoro) vinyl-cyclopropane-carboxylate.

16 g of a mixture of cis and trans isomers (cis:trans ratio of about 80:20) of ethyl 2,2-dimethyl-3-($\beta$-trifluoromethyl-$\beta$-fluoro-vinyl)-cyclopropane carboxylate (obtained by uniting the raw products of preparations analogous with the ones of examples 4, 5, and 7) were distilled at reduced pressure and the following fractions were collected:

I fraction which distilled between 82° and 85° C. at 18 mm Hg (10 g)
II fraction which distilled between 85° and 88° C. at 18 mm Hg (2 g)
III fraction which distilled between 88° and 90° C. at 18 mm Hg (1 g).

The NMR characterization of the individual fractions indicated that fraction I consisted of the pure cis isomer, fraction II consisted of the pure trans isomer while fraction III was a mixture of cis and trans isomers.

(Signals $^1$H and $^{19}$F-NMR and the corresponding couplings were in accordance with the data relating to the corresponding pyrethroid esters indicated in British patent application No. 2,015,519).

What we claim is:

1. A stereoselective process for preparing lower alkyl esters of the cis-2,2-dimethyl-3-($\beta$-trifluoromethyl-$\beta$-trifluorovinyl)-cyclopropane carboxylic acid of the formula:

$$\begin{array}{c} H_3C \diagdown \diagup CH_3 \\ F_3C \diagdown C \diagup \\ \diagdown C=CH-CH\text{———}CH-COOR \\ F \diagup \end{array} \quad \text{(II-F)}$$

wherein R is a $C_1$–$C_4$ alkyl, wherein a compound of the formula $$CF_3-\underset{\underset{Y}{|}}{\overset{\overset{F}{|}}{C}}-CH_2-\underset{\underset{Br}{|}}{CH}-C(CH_3)_2-CH_2-COOR \quad \text{(III-F)}$$

wherein R is a $C_1$–$C_4$ alkyl and Y is chlorine or bromine, is monodehydrohalogenated in the presence of a primary or secondary amine and in a non-polar or low polarity solvent, to selectively obtain a compound of formula:

$$CF_3-\underset{\underset{Y}{|}}{\overset{\overset{F}{|}}{C}}-CH=CH-C(CH_3)_2-CH_2-COOR \quad \text{(A')}$$

and subsequently dehydrohalogenating said product by the action of an alkaline base in a non-polar solvent or in ether maintaining, in the latter case, a temperature below 50° C.

2. A process according to claim 1, for preparing compounds of the formula:

$$CF_3-\underset{\underset{Y}{|}}{\overset{\overset{F}{|}}{C}}-CH=CH-C(CH_3)_2-CH_2-COOR \quad \text{(A')}$$

wherein a compound of formula:

$$CF_3-\underset{\underset{Y}{|}}{\overset{\overset{F}{|}}{C}}-CH_2-\underset{\underset{Br}{|}}{CH}-C(CH_3)_2-CH_2-COOR \quad \text{(III-F)}$$

is dehydrohalogenated in the presence of an at least equimolecular amount of a primary or secondary amine and in a non-polar solvent, R and Y being as defined in claim 1.

3. A process according to claim 2, wherein the dehydrohalogenation of compound III-F is effected by employing an amine selected from piperidine, morpholine, pyrrolidine and n-butylamine.

4. A process according to claim 2, wherein the dehydrohalogenation of compound III-F is effected in a non-polar solvent selected from the group consisting of aliphatic, alicyclic, aromatic and alkylaromatic hydrocarbons.

5. A process according to claim 2, characterized in that the dehydrohalogenation of compound III-F is effected in a low polarity solvent selected from an ether or an alcohol.

6. A process according to claim 1, characterized in that the dehydrohalogenation of compound III-F is effected at a temperature ranging from 0° C. to the boiling temperature of the solvent.

7. A process according to claim 2, characterized in that the dehydrohalogenation of compound III-F is effected in the presence of at least stoichiometric amounts of an amine selected from piperidine, morpholine, pyrrolidine and n-butylamine, in a non-polar solvent and at the boiling temperature of the solvent.

8. A process according to claim 1, for stereoselectively preparing the cis isomers of the compounds of formula:

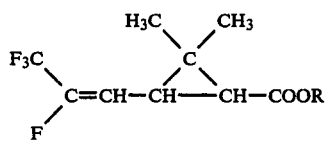

wherein a compound of formula:

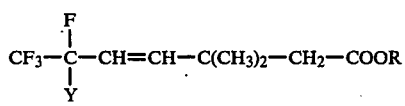

is dehydrohalogenated in the presence of an at least equimolecular amount of an alkaline base, in a non-polar solvent or in an ether maintaining, in the latter case, a temperature below 50° C.

9. A process according to claim 8, wherein the dehydrohalogenation of compound A' is effected by employing as a base an alkaline alcoholate or an alkaline hydride in the presence of lower alcohols.

10. A process according to claim 8, characterized in that the dehydrohalogenation of compound A' is effected in a non-polar solvent selected from the group consisting of aliphatic, alicyclic, aromatic and alkylaromatic hydrocarbons.

11. A process according to claim 10, characterized in that the dehydrohalogenation of compound A' is effected at a temperature ranging from 0° C. to the boiling temperature of the solvent.

12. A process according to claim 8, characterized in that the dehydrohalogenation of compound A' is effected by employing as a solvent an ether and operating at a temperature lower than 50° C.

13. A process according to claim 8, characterized in that the dehydrohalogenation reaction of compound A' is effected by employing an alkaline base, an alcoholate or an alkaline hydride in the presence of a catalytic amount of an alcoholate, in an at least stoichiometric amount in respect of compound A', in a non-polar solvent and at the reflux temperature of the solvent.

14. A process according to claim 1, characterized in that the monodehydrohalogenation of compound III-F to compound A' and the dehydrohalogenation of compound A' to compound II-F is effected without isolating compound A'.

15. A process according to claim 14, characterized in that compound III-F is reacted with an amine selected from piperidine, morpholine, pyrrolidine and n-butylamine in the presence of an alkaline base, in a non-polar solvent, at the boiling temperature of the solvent, whereupon to the resulting mixture there is added an alcoholate or an alkaline hydride and the reaction is carried out at the boiling temperature of the solvent.

* * * * *